United States Patent
Matsumura

(10) Patent No.: US 10,029,980 B2
(45) Date of Patent: Jul. 24, 2018

(54) METHOD FOR PRODUCING METHIONINE

(71) Applicant: Sumitomo Chemical Company, Limited, Chuo-ku, Tokyo (JP)

(72) Inventor: Kana Matsumura, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 15/514,039

(22) PCT Filed: Sep. 16, 2015

(86) PCT No.: PCT/JP2015/076234
§ 371 (c)(1),
(2) Date: Mar. 24, 2017

(87) PCT Pub. No.: WO2016/047516
PCT Pub. Date: Mar. 31, 2016

(65) Prior Publication Data
US 2017/0275247 A1 Sep. 28, 2017

(30) Foreign Application Priority Data

Sep. 26, 2014 (JP) ................................ 2014-196208

(51) Int. Cl.
*C07C 319/20* (2006.01)

(52) U.S. Cl.
CPC .................. *C07C 319/20* (2013.01)

(58) Field of Classification Search
None
See application file for complete search history.

(56) References Cited

U.S. PATENT DOCUMENTS

| 2,542,768 A | 2/1951 | Gresham et al. |
| 4,064,159 A | 12/1977 | Labat et al. |
| 4,960,932 A | 10/1990 | Gillonnier et al. |
| 5,672,745 A | 9/1997 | Hasseberg et al. |
| 6,417,395 B1 | 7/2002 | Ponceblanc et al. |
| 7,670,986 B2 | 3/2010 | Weigel et al. |
| 2010/0197965 A1* | 8/2010 | Belliere-Baca ......... B01J 23/10 562/606 |

FOREIGN PATENT DOCUMENTS

| DE | 102005047597 A1 | 4/2007 |
| FR | 2750987 A1 | 1/1998 |
| JP | S52053816 A | 4/1977 |
| JP | S5446717 A | 4/1979 |
| JP | S62132853 A | 6/1987 |
| JP | 03-093754 A | 4/1991 |
| JP | H03093757 A | 4/1991 |
| JP | H08502277 A | 3/1996 |
| JP | 2003522815 A | 7/2003 |
| JP | 2009511241 A | 3/2009 |
| JP | 2010535182 A | 11/2010 |
| WO | 0160789 A1 | 8/2001 |
| WO | 0160790 A1 | 8/2001 |

OTHER PUBLICATIONS

Tamura et al, "Efficient and Substrate-Specific Hydration of Nitriles to Amides in Water by Using a CeO2 Catalyst," Chemistry: A European Journal, vol. 17, pp. 11428-11431 (2011).
Int'l Search Report dated Dec. 15, 2015 in Int'l Application No. PCT/JP2015/076234.
Search Report dated Nov. 29, 2017 in SG Application No. 11201701863V.
Extended European Search Report dated Apr. 19, 2018 in EP Application No. 15845276.3.

* cited by examiner

*Primary Examiner* — Clinton A Brooks
(74) *Attorney, Agent, or Firm* — Panitch Schwarze Belisario & Nadel LLP

(57) ABSTRACT

A method for producing methionine involves contacting 2-amino-4-(methylthio)butanenitrile with water in the presence of an oxide catalyst containing cerium. The 2-amino-4-(methylthio)butanenitrile may be 2-amino-4-(methylthio)butanenitrile, produced by contacting 2-hydroxy-4-(methylthio)butanenitrile with ammonia water or 2-amino-4-(methylthio)butanenitrile, produced by contacting 3-(methylthio)propionaldehyde with hydrocyanic acid and ammonia water.

6 Claims, No Drawings

METHOD FOR PRODUCING METHIONINE

CROSS-REFERENCE TO RELATED APPLICATION

This application is a Section 371 of International Application No. PCT/JP2015/076234, filed Sep. 16, 2015, which was published in the Japanese language on Mar. 31, 2016 under International Publication No. WO 2016/047516 A1, and the disclosure of which is incorporated herein by reference.

TECHNICAL FIELD

The present invention relates to a method for producing methionine in one step using 2-amino-4-(methylthio)butanenitrile as a raw material.

BACKGROUND ART

As a method for producing methionine, a method for producing methionine by hydrolyzing 2-amino-4-(methylthio)butanenitrile represented by formula (1) has been known for a long time. However, when a strong base is used as the hydrolysis condition, inorganic salts such as carbonates or sulfates are produced at the stage of neutralization after completion of the reaction, and thus a purification step so as to remove salts is required to obtain methionine. A condition without using a strong base has been studied as the hydrolysis condition of 2-amino-4-(methylthio)butanenitrile. However, in order to obtain methionine in good yield, the reaction should be performed under different reaction conditions since a condition for obtaining 2-amino-4-(methylthio)butanenitrile (methionine amide) represented by formula (2) from 2-amino-4-(methylthio)butanenitrile differs from a condition for obtaining methionine from methionine amide (see Patent Document 1). Therefore, this is not always a simple production method.

Although there has also been known a method for directly obtaining amino acid by reacting α-aminonitrile with water in the presence of zinc metal or zinc oxide (see Patent Document 2), the yield of methionine is not always satisfactory.

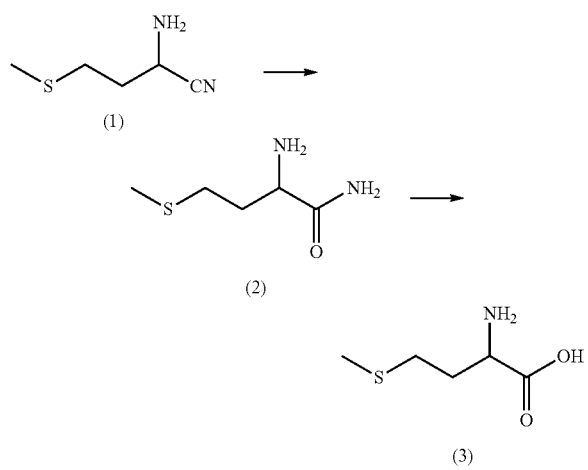

PRIOR ART DOCUMENT

Patent Document

Patent Document 1: JP 2003-522815 W
Patent Document 2: JP 54-46717 A

DISCLOSURE OF THE INVENTION

Problems to be Solved by the Invention

An object of the present invention is to provide a method for simply producing methionine from 2-amino-4-(methylthio)butanenitrile in good yield.

Means for Solving the Problems

The present inventors have intensively studied and found that methionine can be produced in good yield by contacting 2-amino-4-(methylthio)butanenitrile and water with each other in the presence of an oxide catalyst containing cerium, thus completing the present invention.

That is, the present invention includes the following aspects.
1. A method for producing methionine, which comprises the step of contacting 2-amino-4-(methylthio)butanenitrile and water with each other in the presence of an oxide catalyst containing cerium.
2. The production method according to the above item 1, wherein the oxide catalyst containing cerium is at least one selected from the group consisting of cerium oxide and an oxide solid solution containing cerium.
3. The production method according to the above item 1 or 2, wherein the step is performed at 0 to 300° C.
4. The production method according to any one of the above items 1 to 3, wherein 2-amino-4-(methylthio)butanenitrile and water are brought into contact with each other in the presence of ammonia.
5. The production method according to any one of the above items 1 to 4, wherein the 2-amino-4-(methylthio)butanenitrile is 2-amino-4-(methylthio)butanenitrile produced by contacting 2-hydroxy-4-(methylthio)butanenitrile and ammonia water with each other.
6. The production method according to any one of the above items 1 to 4, wherein the 2-amino-4-(methylthio)butanenitrile is 2-amino-4-(methylthio)butanenitrile produced by contacting 3-(methylthio)propionaldehyde, hydrocyanic acid, and ammonia water with each other.

Effects of the Invention

According to the production method of the present invention, methionine can be produced from 2-amino-4-(methylthio)butanenitrile in a simple step in good yield.

MODE FOR CARRYING OUT THE INVENTION

According to the present invention, methionine can be produced by contacting 2-amino-4-(methylthio)butanenitrile and water with each other in the presence of an oxide catalyst containing cerium.

Examples of the oxide catalyst containing cerium include an oxide containing cerium (Ce) as well as a mixed oxide containing cerium and an oxide solid solution containing cerium.

Examples of the oxide containing cerium (Ce) include cerium oxide. Examples of the cerium oxide include cerium (III) oxide ($Ce_2O_3$), cerium(IV) oxide ($CeO_2$), mixtures thereof, or cerium oxide compounds having these mixed phases. Of these, cerium(IV) oxide $CeO_2$ is preferable.

Examples of the oxide solid solution containing cerium include $CeO_2$—$ZrO_2$ (ceria-zirconia), $CeO_2$—$Y_2O_3$, and $CeO_2$—$La_2O_3$, and there is no limitation on the components which are solid-soluted in the cerium oxide, and three or more types of metals may be contained, and of these, ceria-zirconia is most preferable.

As the oxide containing cerium, cerium oxide and an oxide solid solution containing cerium are preferable, and cerium oxide is more preferable.

The content of cerium in the oxide catalyst containing cerium is preferably 5 to 100% by weight, more preferably 30 to 100% by weight, still more preferably 70 to 100% by weight, and yet more preferably 95 to 100% by weight as cerium oxide ($CeO_2$).

The oxide catalyst containing cerium may be used as a mixture with other catalysts. Examples of other catalysts include, but are not particularly limited to, oxides such as zirconium oxide, magnesium oxide, zinc oxide, and titanium oxide, and clay minerals such as hydrotalcite, and of these, zirconium oxide is preferable.

With respect to the oxide catalyst containing cerium, two or more types of catalysts having different composition and physical properties (e.g., form and particle size) may be used in combination. The average particle size of a powdery catalyst is preferably 500 nm or less, more preferably 100 nm or less, and still more preferably 20 nm or less. The specific surface area of a catalyst measured by the BET method is preferably 10 to 2,000 $m^2$/g, more preferably 50 to 1,000 $m^2$/g, and still more preferably 100 to 500 $m^2$/g. As the oxide containing cerium, a commercially available product may be used. For example, an oxide prepared by a method in which a precursor containing cerium compounds is calcined under atmosphere of oxidizing gases such as air may be used. Examples of the precursor containing cerium compounds include cerium compounds and supports impregnated with cerium compounds. Examples of the cerium compounds include halides, inorganic salts (e.g., sulfates, nitrates, carbonates, and phosphates), acetates, oxalates, and hydroxides of cerium. The oxide catalyst containing cerium may be, for example, an oxide containing cerium supported by a support or an oxide containing cerium supporting other components.

The oxide catalyst containing cerium may be heat-treated by, for example, oxidizing gases such as air; inert gases such as nitrogen and argon; reducing gases such as hydrogen; carbon dioxide; steam; or the like. The treatment temperature is not particularly limited, and is preferably 200 to 900° C., and more preferably 400 to 800° C.

As the oxide containing cerium and the oxide catalyst containing cerium, a processed formed product such as a pellet may be used. The formed product can be prepared, for example, in the following step: water, etc. added to a powdery cerium compound, a mixture of the compound with a solid support, or a product supporting both to make a paste, and then the paste is extruded, and the pelleted formed product thus obtained is calcined.

A method for producing 2-amino-4-(methylthio)butanenitrile to be used is not necessarily limited, and usually [Process A] 2-amino-4-(methylthio)butanenitrile produced by contacting 2-hydroxy-4-(methylthio)butanenitrile and ammonia water with each other is used, or [Process B] 2-amino-4-(methylthio)butanenitrile produced by contacting 3-(methylthio)propionaldehyde, hydrocyanic acid (hydrogen cyanide), and ammonia water with each other is used.

In the step of producing methionine in which 2-amino-4-(methylthio)butanenitrile and water are brought into contact with each other, the theoretically necessary amount of water based on 1 mol of 2-amino-4-(methylthio)butanenitrile is 2 mols, but usually an excess amount higher than the theoretical amount is used. Preferably, water in an amount necessary for dissolution of 2-amino-4-(methylthio)butanenitrile is used. Specifically, the amount of water is 0.5 to 10 parts by weight, and more preferably 2 to 5 parts by weight, based on 1 part by weight of 2-amino-4-(methylthio)butanenitrile.

In the above step, water is usually used in the solvent amount, and if necessary, an organic solvent mixed with or without water may be used. Examples of the solvent mixed with water include ether solvents such as 1,4-dioxane and tetrahydrofuran; N-methylpyrrolidinone; N-ethylpyrrolidinone; 1,3-dimethyl-2-imidazolidinone; dimethyl sulfoxide; and acetone.

In terms of the stability of 2-amino-4-(methylthio)butanenitrile in the water solvent, in the step of producing methionine in which 2-amino-4-(methylthio)butanenitrile and water are brought into contact with each other, ammonia is preferably dissolved in advance in the system.

The amount of the oxide containing cerium used is usually 0.0010 to 5.0 mols, more preferably 0.010 to 3.0 mols, and still more preferably 0.020 to 1.50 mols, in terms of cerium, based on 1 mol of 2-amino-4-(methylthio)butanenitrile.

The step of contacting 2-amino-4-(methylthio)butanenitrile and water with each other is usually performed at 0 to 300° C., preferably 40 to 150° C., and more preferably 50 to 110° C. The step may be performed under pressure. In this case, the reaction is preferably permed under increased pressure of 0.1 MPa to 2 MPa, and more preferably 0.2 MPa to 0.5 MPa, in terms of absolute pressure. The step may be performed in any one of a continuous reactor, a semicontinuous reactor, and a batch reactor.

After completion of the reaction, the catalyst is filtered from the reaction mass, and then by-produced ammonia is removed by atmospheric concentration or vacuum concentration, thereby, an aqueous methionine solution can be obtained, and a solid of methionine can also be obtained by further concentration. The solid of methionine thus obtained can also be obtained as high-purity methionine by subjecting to recrystallization.

The catalyst having decreased activity by the reaction may be used after being separated from the reaction mass and regenerated. As a method for regeneration, a method of washing or heat treatment can be used. Washing can be performed with, for example, water, acid, alkali, an organic solvent, and the like. A heat treatment is usually performed under atmosphere of oxidizing gases such as air; inert gases such as nitrogen and argon; reducing gases such as hydrogen; carbon dioxide; steam; or the like. With respect to the atmosphere of the heat treatment, the heat treatment is preferably performed under oxidizing gas atmosphere. The temperature of the heat treatment is preferably 200 to 800° C., and more preferably 300 to 600° C. These methods for washing and heat treatment may be used in combination.

Examples of the method for producing 2-amino-4-(methylthio)butanenitrile include, in addition to Process A and Process B mentioned above, a method for producing 2-amino-4-(methylthio)butanenitrile by contacting acrolein and hydrocyanic acid with each other and then reacting with methyl mercaptan.

Next, Process A will be described.

The amount of ammonia is usually within a range of 1 to 10 mols based on 1 mol of 2-hydroxy-4-(methylthio)butanenitrile. The reaction temperature is usually within a range of 10 to 80° C. As the solvent, water is usually used, and after completion of the reaction, 2-amino-4-(methylthio)butanenitrile is obtained as an aqueous solution. If necessary, deammoniation or partial concentration is performed to obtain an aqueous solution containing 2-amino-4-(methylthio)butanenitrile, and the aqueous solution thus obtained can be used as a raw material in the method for producing methionine of the present invention.

Next, Process B will be described.

The amount of hydrocyanic acid is usually within a range of 1 to 2 mols, and the amount of ammonia is within a range of 1 to 10 mols, based on 1 mol of 3-(methylthio)propionaldehyde. The reaction temperature is usually within a range of 10 to 80° C. As the solvent, water is usually used, and after completion of the reaction, 2-amino-4-(methylthio)butanenitrile is obtained as an aqueous solution. If necessary, deammoniation or partial concentration is performed to obtain an aqueous solution containing 2-amino-4-(methylthio)butanenitrile, and the aqueous solution thus obtained can be used as a raw material in the method for producing methionine of the present invention.

EXAMPLES

The present invention will be described in more detail below by way of Examples, but the present invention is not limited to the following Examples.

Example 1

Preparation of 2-amino-4-(methylthio)butanenitrile from 2-hydroxy-4-(methylthio)butanenitrile In a 1 L three-necked flask equipped with a stirrer, a thermometer, and a dropping funnel, 72.00 g (4.00 mols) of water and 304.11 g (5.00 mols) of 28% ammonia water were charged, and then 142.52 g (1.00 mol) of 2-hydroxy-4-(methylthio)butanenitrile was added dropwise through a dropping funnel over 20 minutes in a state of being heated to 45° C. After completion of the dropwise addition, the solution was stirred at 45° C. for one hour to obtain 2-amino-4-(methylthio)butanenitrile with a reaction yield of 88.0%. The aqueous 2-amino-4-(methylthio)butanenitrile solution thus obtained was used as a raw material for the subsequent step without being purified.

Production of methionine (amount of $CeO_2$ used: 1.27 mols, and in the following Examples, the amount of $CeO_2$ used represents the amount of $CeO_2$ used per 1 mol of 2-amino-4-(methylthio)butanenitrile)

To a tantalum reaction vessel equipped with a thermocouple and a stirrer, 15.0 g (87.15 mmols) of cerium oxide (manufactured by Wako Pure Chemical Industries, Ltd.) and 45.0 g (68.69 mmols) of the aqueous 2-amino-4-(methylthio)butanenitrile solution obtained by the above method were added, followed by stirring at 100° C. for one hour. Then, cerium oxide was removed with a membrane filter, and the reaction solution thus obtained was analyzed by liquid chromatography. As a result, the reaction yield of methionine was 93.2%.

Example 2

Production of Methionine (The Amount of $CeO_2$ Used: 0.58 mol)

In a two-necked flask equipped with a stirrer and a thermometer, 0.7 g (4.07 mmols) of cerium oxide (manufactured by Kanto Chemical Co., Inc.) and 4.7 g of water were charged, and then 4.7 g (7.02 mmols) of the aqueous 2-amino-4-(methylthio)butanenitrile solution obtained by the method of Example 1 was added, followed by stirring at 75° C. for 2 hours. Then, cerium oxide was removed with a membrane filter and the reaction solution thus obtained was analyzed by liquid chromatography. As a result, the reaction yield of methionine was 95.2%.

Example 3

Production of Methionine (Amount of $CeO_2$ Used: 2.04 mols)

In a two-necked flask equipped with a stirrer and a thermometer, 5.2 g (30.21 mmols) of cerium oxide (manufactured by Wako Pure Chemical Industries, Ltd.) and 9.6 g of water were charged, and then 9.6 g (14.78 mmols) of the aqueous 2-amino-4-(methylthio)butanenitrile solution obtained by the method of Example 1 was added, followed by stirring at 75° C. for 2 hours. Then, cerium oxide was removed with a membrane filter and the reaction solution thus obtained was analyzed by liquid chromatography. As a result, the reaction yield of methionine was 92.6%.

Example 4

Production of Methionine (Use of Recovered $CeO_2$)

In a two-necked flask equipped with a stirrer and a thermometer, 5.1 g (29.63 mmols) of the cerium oxide recovered in Example 3 and 9.5 g of water were charged, and then 9.5 g (14.22 mmols) of the aqueous 2-amino-4-(methylthio)butanenitrile solution obtained by the method of Example 1 was added, followed by stirring at 75° C. for 2 hours. Then, cerium oxide was removed with a membrane filter and the reaction solution thus obtained was analyzed by liquid chromatography. As a result, the reaction yield of methionine was 97.0%.

Example 5

Preparation of 2-amino-4-(methylthio)butanenitrile from 3-(methylthio)propionaidehyde In a 500 mL three-necked flask equipped with a stirrer and a thermometer, 29.71 g (1.10 mmols) of hydrocyanic acid, 182.46 g (3.00 mmols) of 28% ammonia water, and 104.17 g (1.00 mol) of 3-(methylthio)propionaldehyde were charged, followed by stirring at 45° C. for one hour to obtain 314.3 g of a reaction mixture. Then, the reaction mixture was analyzed by liquid chromatography. As a result, the content of 2-amino-4-(methylthio)butanenitrile was 39.6%.

Use of deammoniated 2-amino-4-(methylthio)butanenitrile

In 20.03 g of the reaction mixture prepared by the method, nitrogen was bubbled at a rate of 1.15 L/min for 2 hours to remove ammonia. As a result, the content of ammonia decreased from 8.84% to 0.07%, the reaction solution was concentrated to 16.55 g and the content of 2-amino-4-(methylthio)butanenitrile was 41.8%.

In a two-necked flask equipped with a stirrer and a thermometer, 1.38 g (8.02 mmols) of cerium oxide (specific surface area 159.6 m$^2$/g, manufactured by Daiichi Kigenso Kagaku Kogyo Co., Ltd.) and 5 g of water were charged, and then 5 g (16.0 mmols) of the aqueous 2-amino-4-(methylthio)butanenitrile solution deammoniated was added, followed by stirring at 75° C. for 2 hours. Then, the cerium oxide was removed with a membrane filter and the reaction solution thus obtained was analyzed by liquid chromatography. As a result, the reaction yield of methionine was 80.0%.

Example 6

Production of Methionine (Cerium Oxide)

In a two-necked flask equipped with a stirrer and a thermometer, 1.3 g of cerium oxide (specific surface area 159.6 m$^2$/g, manufactured by Daiichi Kigenso Kagaku Kogyo Co., Ltd.) and 4.1 g of water were charged, and then 4.1 g (12.5 mmols) of the aqueous 2-amino-4-(methylthio)butanenitrile solution obtained by the method of Example 5 was added, followed by stirring at 75° C. for 2 hours. Then, the cerium oxide was removed with a membrane filter and the reaction solution thus obtained was analyzed by liquid chromatography. As a result, the reaction yield of methionine was 94.4%.

Example 7

Production of Methionine (Ceria-zirconia; 78 wt % CeO$_2$-22 wt % ZrO$_2$)

The same reaction in Example 6 was performed, except that a ceria-zirconia solid solution (78 wt % CeO$_2$-22 wt % ZrO$_2$, specific surface area 72.0 m$^2$/g, manufactured by Daiichi Kigenso Kagaku Kogyo Co., Ltd.) was used in place of cerium oxide and the amount of 2-amino-4-(methylthio)butanenitrile was changed to 12.7 mmols. The reaction yield of methionine was 94.5%.

Example 8

Production of Methionine (Ceria-zirconia; 40 wt % CeO$_2$-60 wt % ZrO$_2$)

The same reaction as in Example 6 was performed, except that a ceria-zirconia solid solution (40 wt % CeO$_2$-60 wt % ZrO$_2$, specific surface area 54.1 m$^2$/g, manufactured by Daiichi Kigenso Kagaku Kogyo Co., Ltd.) was used in place of cerium oxide and the amount of 2-amino-4-(methylthio)butanenitrile was changed to 12.6 mmols. The reaction yield of methionine was 92.5%.

Example 9

Production of Methionine (Cerium Oxide)

The same reaction as in Example 6 was performed, except that the amount of cerium oxide was changed to 0.22 g (specific surface area 159.6 m$^2$/g, manufactured by Daiichi Kigenso Kagaku Kogyo Co., Ltd.) and the amount of 2-amino-4-(methylthio)butanenitrile was changed to 11.6 mmols. The reaction yield of methionine was 60.9%.

Example 10

Production of Methionine (Use of Cerium Oxide and Zirconium Oxide in Combination)

The same reaction as in Example 6 was performed, except that 0.22 g of cerium oxide (specific surface area 159.6 m$^2$/g, manufactured by Daiichi Kigenso Kagaku Kogyo Co., Ltd.) and 0.22 g of zirconium oxide (specific surface area 97.3 m$^2$/g, manufactured by Daiichi Kigenso Kagaku Kogyo Co., Ltd.) were used in combination in place of cerium oxide and the amount of 2-amino-4-(methylthio)butanenitrile was changed to 12.8 mmols. The reaction yield of methionine was 80.0%.

Example 11

Production of Methionine (Use of Cerium Oxide and Zirconium Oxide in Combination)

The same reaction as in Example 6 was performed, except that 0.22 g of cerium oxide (specific surface area 159.6 m$^2$/g, manufactured by Daiichi Kigenso Kagaku Kogyo Co., Ltd.) and 0.66 g of zirconium oxide (specific surface area 97.3 m$^2$/g, manufactured by Daiichi Kigenso Kagaku Kogyo Co., Ltd.) were used in combination in place of cerium oxide and the amount of 2-amino-4-(methylthio)butanenitrile was changed to 12.8 mmols. The reaction yield of methionine was 88.6%.

Example 12

Production of Methionine (Use of Air-calcined Cerium Oxide)

Cerium oxide (specific surface area 159.6 m$^2$/g, manufactured by Daiichi Kigenso Kagaku Kogyo Co., Ltd.) was held in a muffle furnace in the atmosphere at 700° C. for 10 hours to perform calcination. The same reaction as in Example 6 was performed, except that 0.22 g of air-calcined cerium oxide was used in place of non-calcined cerium oxide and the amount of 2-amino-4-(methylthio)butanenitrile was changed to 13.0 mmols. The reaction yield of methionine was 67.7%.

Example 13

Production of Methionine (Use of Nitrogen-treated Cerium Oxide)

Cerium oxide (specific surface area 159.6 m$^2$/g, manufactured by Daiichi Kigenso Kagaku Kogyo Co., Ltd.) was held in a tubular furnace under nitrogen feed at 700° C. for 10 hours to perform a nitrogen treatment. The same reaction as in Example 6 was performed, except that 0.22 g of nitrogen-treated cerium oxide was used in place of untreated cerium oxide and the amount of 2-amino-4-(methylthio)butanenitrile was changed to 13.0 mmols. The reaction yield of methionine was 74.1%.

Comparative Example

Comparison with Zinc Oxide

In a two-necked flask equipped with a stirrer and a thermometer, 2.0 g (24.57 mmols) of zinc oxide (particle size 20 nm; manufactured by Kanto Chemical Co., Inc.) and 5.0 g of water were charged, and then 5.0 g (14.08 mmols) of the aqueous 2-amino-4-(methylthio)butanenitrile solution obtained in Example 1 was added, followed by stirring at 65° C. for 4 hours. Then, the zinc oxide was removed with a membrane filter and the reaction solution thus obtained was analyzed by liquid chromatography. As a result, the reaction yield of methionine was 17.0%.

Meanwhile, the same reaction as mentioned above was performed, except the 2.0 g of cerium oxide (particle size 15 to 30 nm; manufactured by Kanto Chemical Co., Inc.) was used in place of 2.0 g of zinc oxide. The reaction yield of methionine was 82.0%.

INDUSTRIAL APPLICABILITY

According to the production method of the present invention, methionine can be obtained from 2-amino-4-(methylthio)butanenitrile in good yield without a complex step.

The invention claimed is:

1. A method for producing methionine, which comprises the step of contacting 2-amino-4-(methylthio)butanenitrile and water with each other in the presence of an oxide catalyst containing cerium.

2. The production method according to claim 1, wherein the oxide catalyst containing cerium is at least one selected from the group consisting of cerium oxide and an oxide solid solution containing cerium.

3. The production method according to claim 1, wherein the step is performed at 0 to 300° C.

4. The production method according to claim 1, wherein 2-amino-4-(methylthio)butanenitrile and water are brought into contact with each other in the presence of ammonia.

5. The production method according to claim 1, wherein the 2-amino-4-(methylthio)butanenitrile is 2-amino-4-(methylthio)butanenitrile produced by contacting 2-hydroxy-4-(methylthio)butanenitrile and ammonia water with each other.

6. The production method according to claim 1, wherein the 2-amino-4-(methylthio)butanenitrile is 2-amino-4-(methylthio)butanenitrile produced by contacting 3-(methylthio)propionaldehyde, hydrocyanic acid, and ammonia water with each other.

* * * * *